United States Patent
Henry et al.

(10) Patent No.: US 11,123,478 B2
(45) Date of Patent: Sep. 21, 2021

(54) FECAL COLLECTION DEVICE, SYSTEM AND METHOD

(71) Applicant: Hollister Incorporated, Libertyville, IL (US)

(72) Inventors: Jerome A Henry, Castlebar (IE); Malford E Cullum, Grayslake, IL (US)

(73) Assignee: Hollister Incorporated, Libertyville, IL (US)

( * ) Notice: Subject to any disclaimer, the term of this patent is extended or adjusted under 35 U.S.C. 154(b) by 427 days.

(21) Appl. No.: 16/075,252

(22) PCT Filed: Apr. 7, 2017

(86) PCT No.: PCT/US2017/026523
§ 371 (c)(1),
(2) Date: Aug. 3, 2018

(87) PCT Pub. No.: WO2017/177093
PCT Pub. Date: Oct. 12, 2017

(65) Prior Publication Data
US 2019/0046718 A1    Feb. 14, 2019

Related U.S. Application Data

(60) Provisional application No. 62/320,002, filed on Apr. 8, 2016.

(51) Int. Cl.
*A61M 3/02* (2006.01)
*A61B 17/22* (2006.01)

(52) U.S. Cl.
CPC ............ *A61M 3/0287* (2013.01); *A61M 3/02* (2013.01); *A61M 3/0279* (2013.01);
(Continued)

(58) Field of Classification Search
CPC .. A61B 2017/22037; A61M 2202/068; A61M 3/02; A61M 3/0279; A61M 3/0283; A61M 3/0287; A61M 3/0295
See application file for complete search history.

(56) References Cited

U.S. PATENT DOCUMENTS

| | | |
|---|---|---|
| 504,424 A | 9/1893 | De Pezzer |
| 724,913 A | 4/1903 | Montgomery |

(Continued)

FOREIGN PATENT DOCUMENTS

| | | |
|---|---|---|
| CN | 1868554 | 11/2006 |
| DE | 115740 | 12/1900 |

(Continued)

OTHER PUBLICATIONS

International Search Report and Written Opinion, counterpart to PCT Appl. No. PCT/US17/26523, dated Jun. 14, 2017.
(Continued)

*Primary Examiner* — Kai H Weng
(74) *Attorney, Agent, or Firm* — Cook Alex Ltd.

(57) ABSTRACT

A fecal collection device includes a barrel with a waste drain conduit attached thereto. A drain opening is defined between passages of the barrel and the waste drain conduit. An irrigation conduit is connected to a source of lavage liquid. A trocar plug has a tapered distal end and moves between insertion, irrigation and flushing positions within the barrel passage. When in the insertion position, the tapered distal end of the trocar plug extends from the distal end of the barrel. When in the irrigation position, the irrigation conduit may provide lavage liquid to the barrel passage while the trocar plug covers a majority of the drain opening. When in a flushing position, the trocar plug covers less of the drain opening than when the trocar plug is in the irrigation position.

17 Claims, 5 Drawing Sheets

(52) U.S. Cl.
CPC ........ *A61M 3/0283* (2013.01); *A61M 3/0295* (2013.01); *A61B 2017/22037* (2013.01); *A61M 2202/068* (2013.01)

(56) References Cited

U.S. PATENT DOCUMENTS

| | | | |
|---|---|---|---|
| 1,286,083 | A | 11/1918 | Pennington |
| 3,592,197 | A | 7/1971 | Cohen |
| 3,916,896 | A | 11/1975 | Ballard |
| 4,067,335 | A | 1/1978 | Silvanov |
| 4,503,843 | A | 3/1985 | Boebel |
| 4,516,578 | A | 5/1985 | Shuffield |
| 5,176,630 | A | 1/1993 | Shilling et al. |
| 5,186,714 | A | 2/1993 | Bourdreault et al. |
| 5,356,391 | A | 10/1994 | Stewart |
| 5,391,159 | A | 2/1995 | Hirsch et al. |
| 5,443,445 | A | 8/1995 | Peters et al. |
| 5,549,657 | A | 8/1996 | Stem et al. |
| 5,662,680 | A * | 9/1997 | Desai ............... A61B 17/00234 600/10 |
| 6,030,361 | A | 2/2000 | Miyashiro |
| 6,168,609 | B1 | 1/2001 | Kamen et al. |
| 6,761,702 | B2 | 7/2004 | Smith |
| 6,808,519 | B2 | 10/2004 | Fanelli et al. |
| 7,147,627 | B2 | 12/2006 | Kim et al. |
| 7,628,775 | B2 | 12/2009 | Adams et al. |
| 7,722,583 | B2 | 5/2010 | Kim et al. |
| 7,988,619 | B2 | 8/2011 | Longo et al. |
| 8,075,540 | B2 | 12/2011 | von Dyck et al. |
| 8,323,255 | B2 | 12/2012 | Martino et al. |
| 8,506,537 | B2 | 8/2013 | Torstensen et al. |
| 8,518,012 | B2 | 8/2013 | Smith |
| 2003/0074018 | A1 | 4/2003 | Torstensen et al. |
| 2004/0260152 | A1 | 12/2004 | Sant et al. |
| 2005/0070933 | A1 | 3/2005 | Leiboff |
| 2005/0277811 | A1 | 12/2005 | Richards et al. |
| 2006/0025728 | A1 | 2/2006 | Leiboff et al. |
| 2006/0025729 | A1 | 2/2006 | Leiboff et al. |
| 2006/0030818 | A1 | 2/2006 | McVey |
| 2006/0052752 | A1 | 3/2006 | McMichael |
| 2007/0073216 | A1 | 3/2007 | McAuliffe et al. |
| 2009/0216206 | A1 | 8/2009 | Nishtala et al. |
| 2009/0326490 | A1 | 12/2009 | McMichael et al. |
| 2010/0185155 | A1 | 7/2010 | McMichael et al. |
| 2010/0280368 | A1 | 11/2010 | Can et al. |
| 2013/0116559 | A1 * | 5/2013 | Levin ................ A61B 1/04 600/437 |
| 2013/0245380 | A1 * | 9/2013 | Vogel ................ A61B 1/32 600/205 |
| 2014/0048556 | A1 * | 2/2014 | Pearcy ............. A61M 5/31511 222/1 |

FOREIGN PATENT DOCUMENTS

| | | |
|---|---|---|
| EP | 1434611 | 6/2006 |
| GB | 2516429 | 1/2015 |
| WO | 1987001596 A1 | 3/1987 |
| WO | WO 2009/015152 A1 | 1/2009 |
| WO | WO 2010/089651 A1 | 8/2010 |
| WO | 2015117141 A1 | 8/2015 |

OTHER PUBLICATIONS http://d11fdyfhxcs9cr.cloudfront.net/templates/156372/myimages/aqualegato_brochure.pdf p. 17 of Brochure: Hydrocare and QMS Disposable Specula.
International Preliminary Amendment on Patentability in corresponding PCT Application No. PCT/US2015/014290 dated Aug. 9, 2016, 8 pages.
International Search Report and Written Opinion for in corresponding PCT Application No. PCT/US2015/014290 dated Jun. 16, 2015, 6 pages.
Australian Office Action dated Sep. 18, 2018 for Application No. 2015210632.
EPO Office Action dated Dec. 6, 2018 for Application No. EP15707196.0.

* cited by examiner

FECAL COLLECTION DEVICE, SYSTEM AND METHOD

CROSS-REFERENCE TO RELATED APPLICATIONS

The present application is the U.S. National Stage of PCT International Patent Application No. PCT/US2017/26523, filed Apr. 7, 2017, which claims the benefit of and priority to U.S. Provisional Application No. 62/320,002, filed Apr. 8, 2016, the contents of both of which are hereby incorporated herein by reference.

FIELD OF THE INVENTION

The present disclosure relates generally to medical waste fluid collection systems and, in particular, to a fecal collection device, system and method for bowel management.

BACKGROUND

Transanal irrigation is a process used by individuals who have bowel management issues, such as incontinence, constipation or other bowel dysfunction. Alternatively, transanal irrigation may be used for regular bowel evacuations by individuals who are incapacitated due to illness or other medical conditions and thus cannot access a toilet. Furthermore, individuals that are bedridden may develop fecal impaction. Such bowel obstructions may be removed via transanal irrigation. During transanal irrigation, water or other lavage fluid is introduced into the rectum and colon through a device positioned through the anus so that feces are flushed and evacuated.

Devices for performing transanal irrigation typically include a tool having a tubular body that defines a central passage. The distal end portion of the tubular body is inserted through the anus and anal canal of a patient so that the open end of the central passage is in communication with the rectum. A pressurized stream of lavage fluid or water is then introduced into the opposite or proximal end of the tool body so as to flow through the central passage of the tool and into the rectum and colon. As a result, the feces within the patient's bowel are loosened, flushed and directed, via the tool, to a collection container or drainage system.

In order to decrease the patient discomfort associated with insertion of the tool through the anus and into the rectum, obturators or plugs having rounded or tapered distal ends may be positioned within the central passage of the tubular body. The rounded or tapered end of the obturator or plug protrudes from the distal end of the tool and the obturator or plug remains installed as the tool is inserted through a patient's anus and anal canal. Once the tool is in position, the obturator or plug is removed from the central passage through the open proximal end of the tool. The pressurized lavage liquid may then be introduced into the rectum and colon.

Obturators or tapered plugs are typically used, however, with tools such as a proctoscope or a speculum. A disadvantage of such devices is that they are designed to permit examination of the anal canal and/or rectum once the obturator or plug is removed. They therefore provide an unsealed opening at the proximal end of the tool that leads to the interior of the bowel when the obturator or plug is removed. As a result, there is no way that lavage fluid may be retained within the bowel for a period of time, which may be desirable during some procedures.

Prior art devices that recognize the above issue have been developed. An example of such a device is disclosed in U.S. Patent Application Publication No. 2013/0245380 to Vogal. The device of Vogal permits a cap to be secured over the opening in the proximal end of the tool after the obturator is removed. Pressurized lavage liquid may then be introduced into the bowel through a side port formed in the barrel of the device. Such an approach, however, requires the user to screw the cap onto proximal end of the tool prior to introduction of the lavage liquid. Attaching the cap, however, may be quite awkward for a user. In addition, the user must keep track of the end cap as a separate part, which could easily become misplaced or lost.

A further disadvantage of the device of U.S. Patent Application Publication No. 2013/0245380 to Vogal is that the irrigation fluid side port must connect to a dedicated line that is connected to the source of lavage liquid. This is in addition to a separate waste drain line that is spaced from the irrigation line. The spaced configuration of the irrigation and drain lines reduces the ease of handling and use of the device and increases the chances that a line will be caught or hung up on something while in use. In addition, the separate irrigation and drainage ports increase the manufacturing cost and complexity of the device.

Alternative devices for flushing of the bowel include a distal end that is inserted into the rectum to simultaneously provide both a lavage liquid supply port and a drain port. Examples of such devices are presented in U.S. Pat. Nos. 6,761,702 and 8,518,012, both to Smith, as well as U.S. Patent Application Publication No. 2006/0025728 to Leiboff et al. A disadvantage of these devices, however, is that there is no way to prevent the lavage liquid from immediately exiting the bowel through the drain port during irrigation. As a result, lavage liquid may not be retained in the bowel for a period of time. Furthermore, a portion of the lavage liquid may exit the bowel immediately upon introduction, which may limit the effectiveness of the procedure. A further disadvantage of the devices of these prior art references is that the lavage fluid supply conduit runs through the central passage of the tool body. As a result, there is no way to provide a obturator or tapered plug to facilitate insertion of the device into the patient's anus and rectum.

Accordingly there continues to be a desire to develop a fecal collection device, system and/or method for bowel management that addresses at least some of the above issues.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a fecal collection device includes a barrel having a distal end and a proximal end. A barrel passage is also defined. A waste drain conduit defining a waste drain passage is attached to the barrel so that a drain opening is defined between the barrel passage and the waste drain passage. An irrigation conduit has a first opening and a second opening, and the second opening is adapted to communicate with a source of lavage liquid. A trocar plug has a tapered distal end and is movably positioned within the barrel passage. The trocar plug is movable between an insertion position, an irrigation position and a flushing position. When in the insertion position, the tapered distal end of the trocar plug extends from the distal end of the barrel. When in the irrigation position, the first opening of the irrigation conduit is in communication with the barrel passage and the trocar plug covers a majority of the drain opening. When in a flushing position, the trocar plug covers less of the drain opening than when the trocar plug is in the irrigation position.

In another aspect, a method for fecal collection includes providing a fecal collection device including a barrel having a distal end, a proximal end and a barrel passage, a waste drain conduit defining a waste drain passage attached to the barrel so that a drain opening is defined between the barrel passage and the waste drain passage, an irrigation conduit having a first opening selectively in communication with the barrel passage and a second opening and a trocar plug having a tapered distal end, where the trocar plug is movably positioned within the barrel passage. The second opening of the irrigation conduit is placed in communication with a source of lavage liquid. The trocar plug is placed in an insertion position where the tapered distal end of the trocar plug extends from the distal end of the barrel. The distal end and a portion of the barrel of the fecal collection device are then inserted into an anal canal of a patient. The trocar plug is then moved into an irrigation position where the first opening of the irrigation conduit is in communication with the barrel passage and the trocar plug covers a majority of the drain opening. Lavage liquid is introduced into a rectum of the patent through the irrigation conduit and the barrel passage of the fecal collection device. The trocar plug is next moved into a flushing position where the trocar plug covers less of the drain opening than when the trocar plug is in the irrigation position. Fecal matter and lavage liquid is then drained from the rectum of the patient through the barrel passage and the waste drain passage of the fecal collection device.

In yet another aspect, a system for fecal collection includes a source of lavage liquid and a fecal collection device. The fecal collection device includes a barrel having a distal end and a proximal end. A barrel passage is also defined. A waste drain conduit defining a waste drain passage is attached to the barrel so that a drain opening is defined between the barrel passage and the waste drain passage. An irrigation conduit has a first opening and a second opening, and the second opening communicates with a source of lavage liquid. A trocar plug has a tapered distal end and is movably positioned within the barrel passage. The trocar plug is movable between an insertion position, an irrigation position and a flushing position. When in the insertion position, the tapered distal end of the trocar plug extends from the distal end of the barrel. When in the irrigation position, the first opening of the irrigation conduit is in communication with the barrel passage and the trocar plug covers a majority of the drain opening. When in a flushing position, the trocar plug covers less of the drain opening than when the trocar plug is in the irrigation position.

BRIEF DESCRIPTION OF THE DRAWINGS

FIGS. 6A-6C show the fecal collection device of FIGS. 1A-1C and 5 being used to flush a patient's bowel in accordance with a method of the present disclosure, where

DETAILED DESCRIPTION OF EMBODIMENTS

Figures 1A, 1B, 1C:
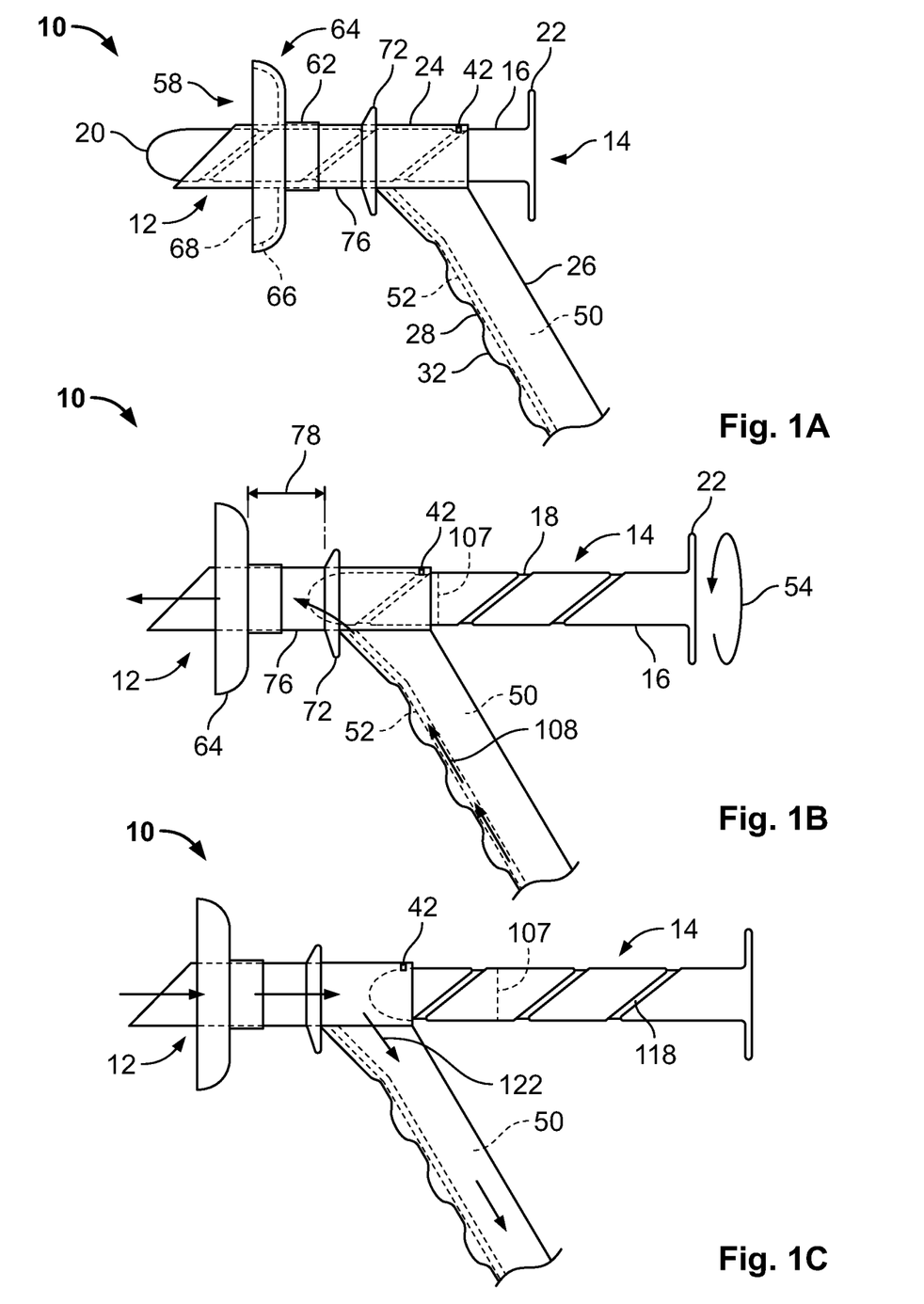
FIG. 1A is a side elevational view of an embodiment of the fecal collection device of the disclosure with the trocar plug in an insertion position where it is fully inserted into the anoscope.
FIG. 1B is a side elevational view of the fecal collection device of FIG. 1A with the trocar plug in an irrigation position where lavage liquid may be introduced into a patient's bowel.
FIG. 1C is a side elevational view of the fecal collection device of FIGS. 1A and 1B with the trocar plug in a flushing position where the fecal matter and lavage liquid may be flushed from the bowel.

An embodiment of the fecal collection device of the disclosure is indicated in general at 10 in FIGS. 1A-1C. The device features two main components: an anoscope, indicated in general at 12, and a trocar plug, indicated in general at 14.

As will be explained in greater detail below, the trocar plug is the movable component of the device. With reference to FIGS. 1A-1C and 2, the trocar plug 14 includes a cylindrical shaft 16 within which a helical groove 18 is formed. The trocar plug also features a tapered distal end 20 and a disc-shaped knob portion 22 positioned on the proximal end. The tapered distal end 20 is shaped to be atraumatic to the anus, sphincter and the anal canal during insertion of the device into a patient.

It is to be understood in that, as used herein, the term "proximal" means nearest to or facing towards the practitioner or other user of the device, while "distal" means furthest away from or facing away from the practitioner or other user and towards the patient. For example, the distal end of the anoscope is the end inserted into the patient and the proximal end is the end which features a handle.

The trocar plug is preferably made from a suitable polymer material, such as polypropylene. Alternative polymer materials or materials that are at least semi-rigid may alternatively be used.

As illustrated in FIGS. 1A-1C, the anoscope features a barrel portion 24 to which is attached a handle portion 26. The handle preferably includes indentations 28 and ribs 32 to provide an ergonomic grip for the user.

Figure 3:
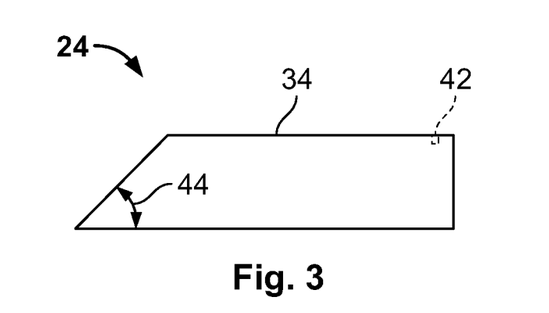
FIG. 3 is a side elevational view of the barrel portion of the anoscope of the fecal collection device of FIGS. 1A-1C.
Figure 4:
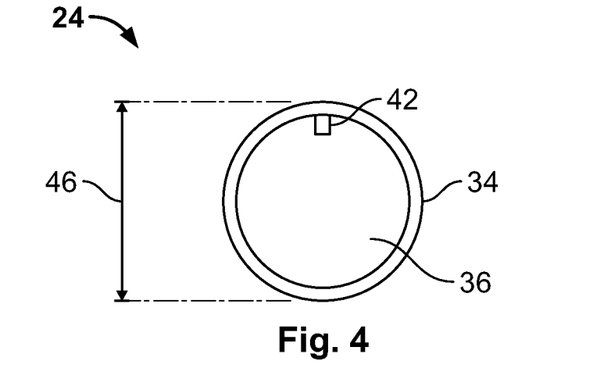
FIG. 4 is an end elevational view of the barrel of FIG. 3.

As illustrated in FIGS. 3 and 4, the barrel portion of the anoscope features a tubular wall 34 which defines a central barrel passage 36. Positioned within the barrel passage, and attached to the inner surface of the tubular wall of the barrel, is a tab 42. While the tab 42 is illustrated at the twelve o'clock position in the proximal end portion of the barrel, it is to be understood that the tab may be located anywhere about, or adjacent to, the circumference of the inner surface of tubular wall 34 and at any location along the length of the barrel central passage.

With reference to FIG. 3, the distal end of the barrel 24 may optionally include a chamfer. With reference to the angle indicated at 44, the chamfer is preferably angled between 22° and 90°, with 45° (illustrated in FIGS. 1A-1C and 3) typically being the optimal chamfer angle to facilitate entry of the distal end of the barrel through the anal canal and accommodate exiting of fecal matter.

The outer diameter of the anoscope barrel, illustrated at 46 in FIG. 4, is preferably similar to clinically available anoscopes and thus, as an example only, is preferably in the range of 11 mm-34 mm.

The handle 26 of the anoscope serves as a waste drain conduit that defines a waste drain passage, indicated at 50 in FIGS. 1A-1C. The top end of the waste drain passage opens into the barrel passage so that a drain opening is formed therebetween. As will be explained in greater detail below, the waste drain passage serves as the drainage port for the device and preferably has a cross sectional area that is approximately the same as the cross sectional area of the barrel passage 36 (FIG. 4). An irrigation conduit, indicated in phantom at 52 in FIGS. 1A-1C, may be positioned within the waste drain passage and has a first open end positioned at or near the drain opening and a second end that is adapted to be connected to a source of lavage liquid, such as water. In alternative embodiments, the irrigation conduit may be positioned with the handle sidewall or it may traverse the exterior of the handle and pass through an opening either in the handle or the barrel. Alternatively, the irrigation conduit may have a dedicated port formed in the handle or the barrel.

In alternative embodiments, the waste drain conduit may be formed independent of the handle so that the handle may be in a position other than what is illustrated in FIGS. 1A-1C and FIGS. 5-6C, or the barrel portion 24 (FIG. 1A) itself may serve as the handle.

The anoscope is preferably molded from a silicon material having a 50-80 durometer hardness or a plastic material. Any alternative material that is at least semi-rigid, however, may be used. The barrel and handle portions may be molded as a single piece or formed in multiple pieces that are joined.

As illustrated in FIGS. 1A-1C, the barrel passage of the anoscope is sized to receive the trocar plug 14 in a manner whereby the trocar plug may be rotated therein. A user may easily turn the trocar plug using the disc-shaped knob portion 22, as indicated by arrow 54 in FIG. 1B. The tab 42 of the anoscope barrel is sized to engage and traverse the helical groove 18 of the trocar plug as the trocar plug is turned. As the user turns the trocar plug knob 22 in a counterclockwise direction (as viewed from the backside of the knob) and the tab 42 traverses the helical groove 18, the trocar plug is advanced towards the distal end of the anoscope barrel, and ultimately into the position illustrated in FIG. 1A. At this point, the tab encounters the proximal end of the helical groove so that a stop is provided and further forward travel of the trocar plug is prohibited. If the trocar plug knob 22 is rotated in the opposite direction (clockwise when viewed from back side of the knob), the tab 42 traverses the helical groove 18 in the opposite direction and the trocar plug is retracted towards the proximal end of the anoscope barrel. The trocar plug travels through the position illustrated in FIG. 1B and ultimately into the position illustrated in FIG. 1C. At this point, the tab encounters the distal end of the helical groove so that a stop is provided. As a result, the trocar plug cannot be removed from the barrel of the anoscope.

In order to minimize leaks of lavage liquid and waste from the anus when the fecal collection device is in use, the barrel of the anoscope is provided with a retention cuff, indicated in general at 58 in FIGS. 1A-1C. The cuff features a central collar portion 62 having a central opening that is sized to circumferentially engage the surface of the anoscope barrel in an interference fit fashion. The attachment may optionally be secured in place with adhesive as well. Any other fastening arrangement known in the art may alternatively be used.

A dish portion 64 surrounds and is circumferentially connected to the collar portion of the retention cuff and features a radially extending sidewall wall 66, illustrated in phantom in FIG. 1A. The sidewall initially extends in a plane generally perpendicular to the surface of the anoscope barrel and then radially curves into an annular lip portion that is generally parallel to the barrel surface. As a result, an annular trough 68 is provided.

In an alternative embodiment, the dish portion 64 of the retention cuff may be directly connected to the anoscope barrel without the use of a collar.

The retention cuff is preferably made from a flexible material, examples of which include, but are not limited to, silicone, rubber or plastic.

An example of a suitable retention cuff is provided in commonly owned PCT International Application No. PCT/US2015/014290, International Publication No. WO 2015/117141, the contents of which are hereby incorporated by reference.

Any alternative retention cuff known in the art may be substituted for the illustrated retention cuff, whether it be inflationless or inflatable. As an example only, in an alternative embodiment, the retention cuff may take the form of an annular balloon that is inflated once the device is properly positioned within the patient's anus and rectum.

A spacer or stop to limit insertion of the device into the patient's rectum is provided on the anoscope barrel, as indicated at 72 in FIGS. 1A-1C. The stop preferably takes the form of an annular flange that is radially tapered on the proximal side to enhance engagement with the anus. The stop may be integrally molded with the anoscope barrel or separately formed and attached thereto, such as by an interference fit, adhesive or any other fastening arrangement known in the art.

The portion of the anoscope barrel between the retention cuff dish 64 and the stop 72 forms a transsphincter section 76 and features a length 78 (shown in FIG. 1B) that is preferably approximately the same length as the transsphincteric zone of the patient.

Figure 5:
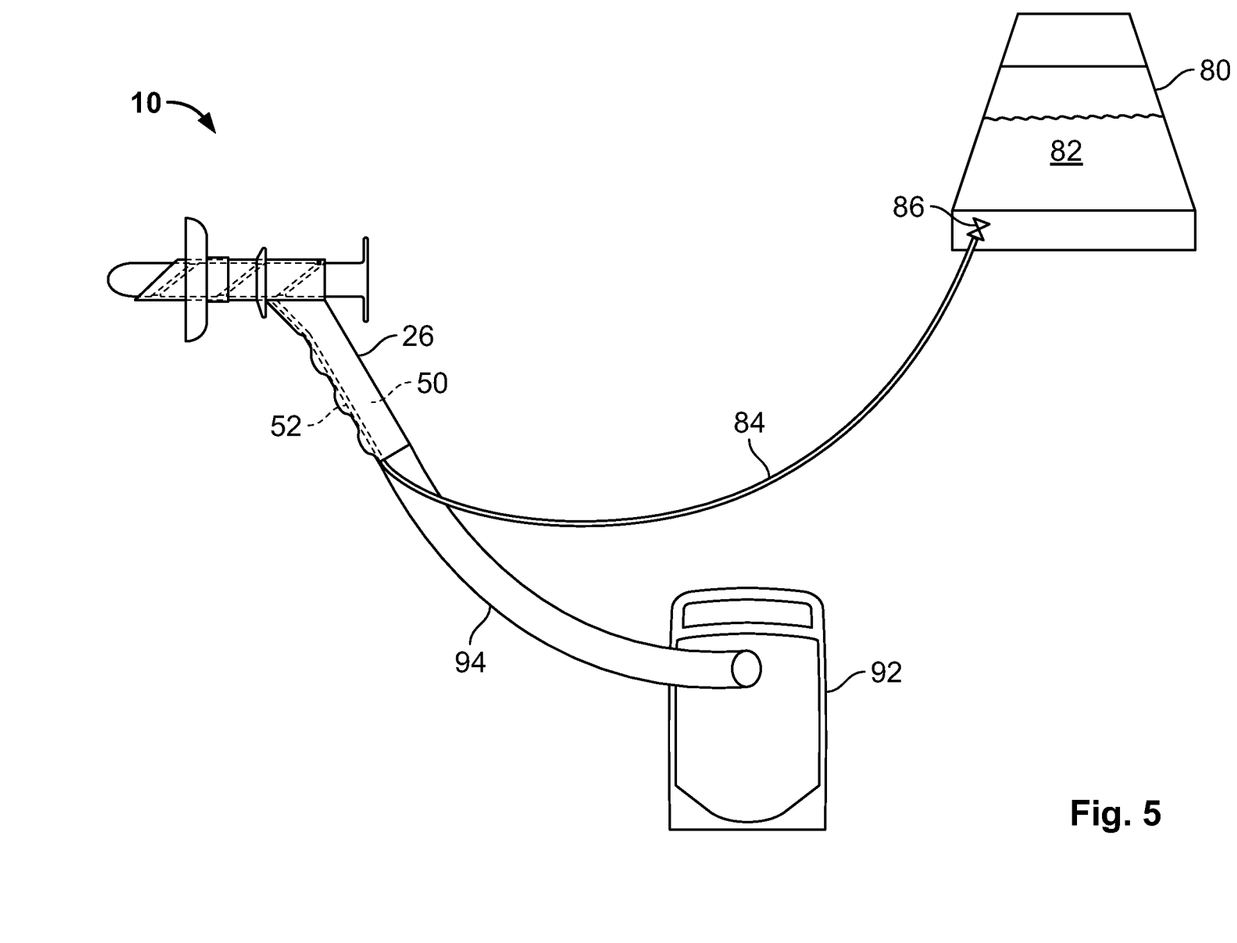
FIG. 5 is a fecal collection system incorporating the fecal collection device of FIGS. 1A-1C.

A system for performing transanal irrigation that incorporates the fecal collection device of FIGS. 1A-4 is illustrated in FIG. 5. A container 80 holding lavage liquid 82, such as water is connected to the irrigation conduit 52 of the device via tubing 84. The container includes a valve 86 which is opened to provide the lavage liquid 82 to the device irrigation conduit 52. The valve may alternatively be placed within line 84. The container 80 is configured to provide pressurized liquid to the device either through gravity or via a pump which may be incorporated into the container or positioned within line 84. The container 80 may be replaced with any other source of pressurized lavage liquid.

A waste collection container 92 is connected to the waste drain passage 50 of the anoscope handle 26 via tubing 94. As an alternative to the waste collection container, the tubing 94 may be positioned within a toilet or waste drainage system.

As is clear from FIG. 5, integrating the irrigation channel 52 into the waste drain passage 50 of the handle 26 permits attachment of both the irrigation liquid tubing 84 and waste drain tubing 94 to the bottom of the handle. This facilitates handling of the device and provides the device with a more compact and visually appealing profile.

Operation of the device of FIGS. 1A-4 and system of FIG. 5 will now be described with reference to FIGS. 1A-1C and 6A-6C.

Figure 6A:
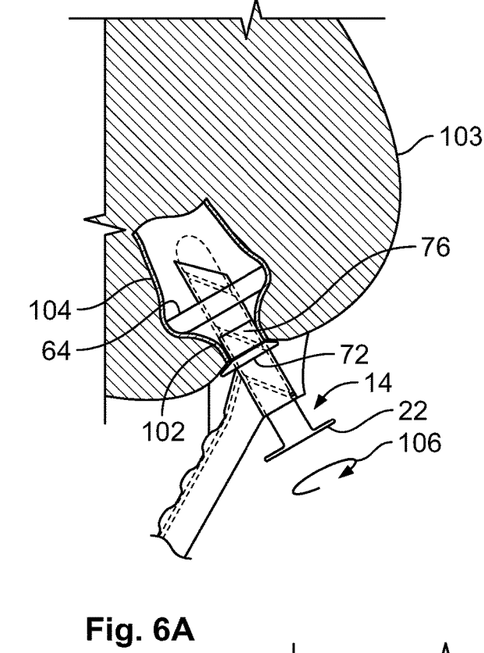
FIG. 6A shows the device after insertion through the patient's anus and anal canal.

The trocar plug 16 is initially placed within the barrel passage of the anoscope in the insertion position illustrated in FIGS. 1A and 6A. With reference to FIG. 6A, the distal portion of the anoscope is then introduced through the anus and anal canal 102 of a patient 103. The retention cuff dish portion 64 radially deforms and collapses about the anoscope barrel as it travels through the anal canal. The insertion continues until the stop 72 of the device engages the anus and the device is in the position illustrated in FIG. 6A. As illustrated in FIG. 6A, when the device is correctly positioned, the transsphincter section 76 of the anoscope barrel is positioned within and engaged by the anal canal 102, and the retention cuff dish portion 64 expands within the rectum 104 so as to be seated against the rectal floor of the patient. The expansion of the retention cuff dish portion 64 as it enters the rectum 104, and the corresponding reduction in insertion force, provides the practitioner with tactile feedback that the device has been properly positioned.

Figure 6B:
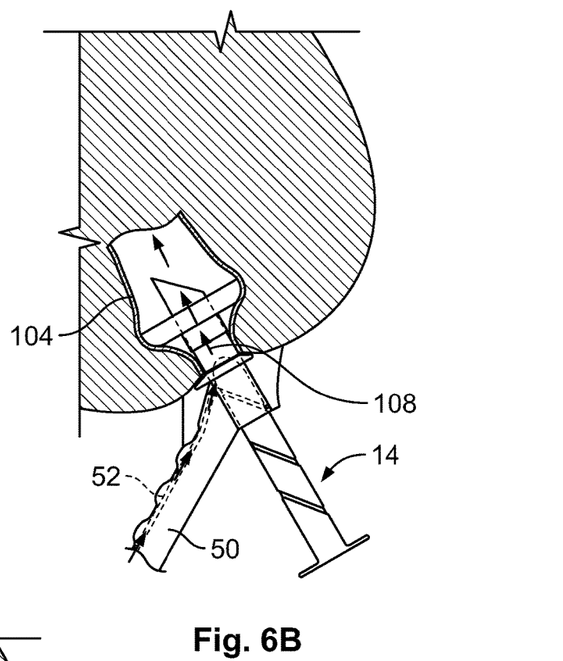
FIG. 6B shows the device being used to introduce pressurized lavage liquid into the bowel and FIG. 6C shows fecal matter and lavage liquid being flushed from the bowel through the device.

Once the fecal collection device is properly positioned, the trocar the knob 22 of the trocar plug 14 is rotated (as illustrated by arrow 106 in FIG. 6A) until the trocar plug is in the irrigation position illustrated in FIGS. 1B and 6B. In this position, the top opening of the irrigation conduit 52 is unobstructed while the majority of the remaining drain opening leading to the waste drain passage 50 of the handle is covered by the distal portion of the trocar plug. As illustrated in FIG. 1B, the trocar plug 14 may be provided with a marking 107 that is exposed when the trocar plug is in the correct position for irrigation. Alternatively, additional resistance may be provided, such as by narrowing the helical groove or providing a rough spot in the helical groove sidewall at the corresponding location, to indicate to the user that the trocar plug is properly positioned for irrigation.

With reference to FIG. 5, the valve 86 of the lavage liquid container is next opened (or the lavage liquid source is otherwise be activated) so that the lavage liquid travels through tubing 84 to the irrigation conduit 52 of the device.

As illustrated by arrows 108 of FIGS. 1B and 6B, the lavage liquid flows up through the irrigation conduit 52, through the barrel passage (36 of FIG. 4) and into the patient's rectum 104 and sigmoid colon so that the cavities are irrigated and fecal matter is softened and dislodged. Because the waste drain passage top opening of the handle is generally covered, the leakage of lavage liquid into the waste drain passage is minimal.

Figure 2:
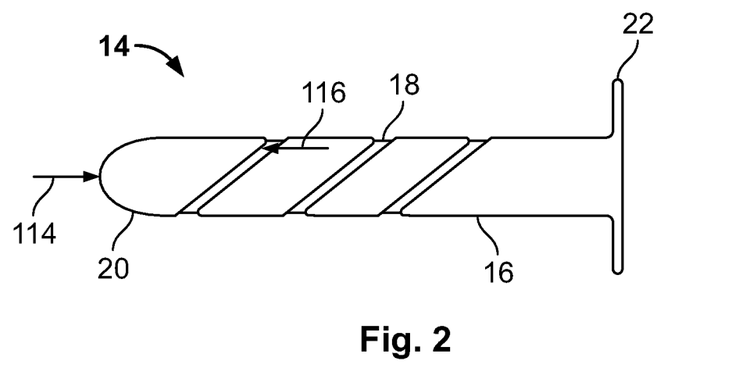
FIG. 2 is a side elevational view of the trocar plug of the fecal collection device of FIGS. 1A-1C prior to installation into the anoscope.

As the pressurized lavage liquid enters the rectum, it will tend to exert a force on the distal tip of the trocar plug, as indicated by arrow 114 of FIG. 2. In response to this force, the tab (42 of FIGS. 3 and 4) exerts a force on the sidewall of the helical groove 18, which includes a component, indicated by arrow 116 of FIG. 2, that opposes the force 114. As a result, the trocar plug stays in the position illustrated in FIGS. 1B and 6B. In addition, the patient could possibly suffer from a rectal spasm during irrigation, which would tend to push the trocar plug out of the anoscope. The force 116 exerted by the tab (42 of FIGS. 3 and 4) on the sidewall of the helical groove 18 also holds the trocar plug in position during such an event.

Figure 6C:
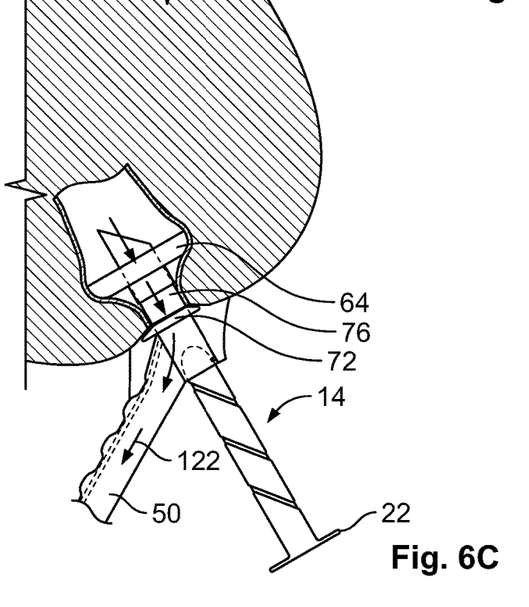

After an appropriate period of time, for example one to two minutes, the knob 22 of the trocar plug is further rotated so that the trocar plug is moved into the flushing position illustrated in FIGS. 1C and 6C. Preferably the tab 42 encounters the proximal end of the helical groove 18 to provide a stop when the trocar plug has reached this position. The flow of lavage liquid through irrigation conduit 52 may be halted prior to this time, at this time or after this time.

When the trocar plug is in the position of FIGS. 1C and 6C, the drain opening leading to the waste drain passage 50 is opened so that the fecal matter and lavage fluid drains from the sigmoid colon and rectum through the barrel passage and waste drain passage 50 of the device as indicated by arrows 122. The drained fecal matter and waste liquid flows from the waste drain passage into tubing 94 (FIG. 5) and into waste container 92, a toilet or any other waste drain system.

If additional irrigation cycles are desired, the knob 22 of the trocar plug may be turned to return the trocar plug to the position illustrated in FIGS. 1B and 6B. The lavage liquid may then again be introduced into the rectum and sigmoid colon, and the above cycle repeated.

The retention cuff 58, rigid transsphinter zone 76 and stop 72 limit leakage of fecal matter and lavage liquid from around the anal canal, thus improving the dignity of the patient by preventing soiling of the patient, bed linen and bed clothes.

Furthermore, in view of the above, the handle 26 of the anoscope is multi-functional in that it (1) has an ergonomic handle which assists a clinician in safely using the device; (2) enables use of the trocar plug as a valve that may be configured to either generally prevent or admit fecal material to exit into the waste containment bag and (3) incorporates an irrigation conduit which delivers lavage liquid to the anal canal so as to soften any feces in the rectum or sigmoid or descending colon.

Figure 7:
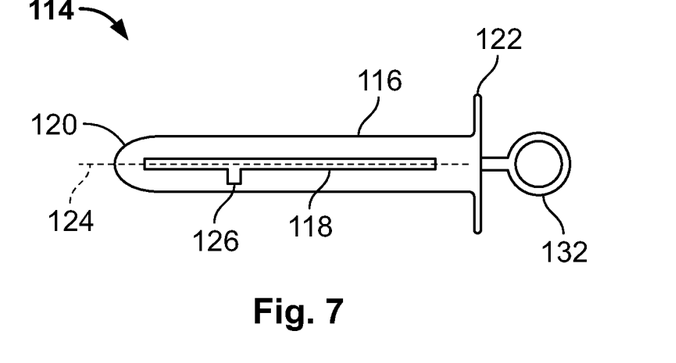
FIG. 7 is a top plan view of the trocar plug in an alternative embodiment of the fecal collection device of the disclosure prior to installation into the anoscope of FIGS. 1A-1C.

An alternative embodiment of the trocar plug that may be used in the anoscope 12 of FIGS. 1A-1C is indicated in general at 114 in FIG. 7. As with the trocar plug 14 of FIGS. 1A-1C and 6A-6C, the trocar plug 114 of FIG. 7 includes a cylindrical shaft 116 with a tapered distal end 120 and a disc-shaped knob portion 122 positioned on the proximal end. In contrast to the helical groove 18 of FIGS. 1A-1C, however, the trocar plug 114 includes an elongated groove 118 that is parallel to the longitudinal axis (illustrated in phantom at 124) of the trocar plug. The elongated groove 118 is provided with a notch 126 that receives the tab (42 in FIGS. 3 and 4) of the anoscope barrel when the trocar plug is in the irrigation position illustrated in FIGS. 1B and 6B. More specifically, when the tab (42 of FIGS. 3 and 4) is positioned within the elongated groove 118, the trocar plug may be freely moved between the positions illustrated in FIGS. 1A-1C. When the trocar plug is in the irrigation position illustrated at 1B and 6B, the knob 122 may be turned so that the tab enters the notch 126 to secure the trocar plug in place against the irrigation liquid pressure and rectal spasm forces described above with reference to FIG. 2. A ring 132 may optionally be added to the proximal side of knob 122 to facilitate longitudinal movement of the trocar plug 114 by the practitioner.

In further alternative embodiments, the tab (42 of FIGS. 3 and 4) of the anoscope barrel and groove in the trocar plug may be eliminated entirely, and the sliding friction between the interior surface anoscope barrel and the outer surface of the trocar plug may be relied upon to hold the trocar plug I the selected position. The retention force may be increased by providing a rough surface (such as by adding ridges, etc.) to the barrel interior surface and/or the outer surface of the trocar plug.

While the preferred embodiments of the disclosure have been shown and described, it will be apparent to those skilled in the art that changes and modifications may be made therein without departing from the spirit of the disclosure, the scope of which is defined by the following claims.

What is claimed is:

1. A fecal collection device comprising:
   a. a barrel having a distal end, a proximal end and defining a barrel passage therebetween; wherein the barrel comprises a tab positioned within the barrel passage;
   b. a waste drain conduit including a waste drain passage attached to the barrel so that a drain opening is defined between the barrel passage and the waste drain passage;
   c. an irrigation conduit having a first opening and a second opening where the second opening is adapted to communicate with a source of lavage liquid;
   d. a trocar plug having a tapered distal end and the trocar plug including a helical groove with a proximal and distal end;
   e. said trocar plug movably positioned within the barrel passage and movable between:
      i) an insertion position where the tapered distal end of the trocar plug extends from the distal end of the barrel;
      ii) an irrigation position where the first opening of the irrigation conduit is in communication with the barrel passage and the trocar plug covers a majority of the drain opening; and
      iii) a flushing position where the trocar plug covers less of the drain opening than when the trocar plug is in the irrigation position; and wherein the helical groove of the trocar plug is traversed by the tab of the barrel as the trocar plug moves between the insertion, irrigation and flushing positions; where the proximal end of the groove serves as a stop when the trocar plug is in the insertion position and the distal end of the groove serves as a stop that prevents removal of the trocar plug from the barrel passage when the trocar plug is in the flushing position.

2. The fecal collection device of claim 1 further comprising a retention cuff positioned on the barrel.

3. The fecal collection device of claim 2 further comprising a spacer positioned on the barrel so that a transsphincter section is defined between the retention cuff and the spacer, said transsphincter section adapted to engage an anal canal of a patient.

4. The fecal collection device of claim 2 wherein the retention cuff is circumferentially positioned on the barrel.

5. The fecal collection device of claim 3 wherein the spacer is an annular flange.

6. The fecal collection device of claim 1 wherein the trocar plug includes a marking that is visible when the trocar plug is in the irrigation position.

7. The fecal collection device of claim 1 wherein the trocar plug includes a proximal end that extends from the proximal end of the barrel, and the proximal end of the trocar plug is provided with a knob.

8. The fecal collection device of claim 1 wherein the trocar plug includes a proximal end, and the proximal end is provided with a ring.

9. The fecal collection device of claim 1 wherein the distal end of the barrel is chamfered.

10. The fecal collection device of claim 1 further comprising a handle attached to the barrel, said handle defining the waste drain conduit.

11. The fecal collection device of claim 10 wherein the irrigation conduit traverses the handle.

12. The fecal collection device of claim 1 wherein the irrigation conduit is positioned within the waste drain passage of the handle.

13. A method for fecal collection comprising the steps of:
   a. providing a fecal collection device including a barrel having a distal end and a barrel passage therebetween, wherein the barrel comprises a tab positioned within the barrel passage; a waste drain conduit defining a waste drain passage attached to the barrel so that a drain opening is defined between the barrel passage and the waste drain passage, an irrigation conduit having a first opening selectively in communication with the barrel passage and a second opening where the second opening is adapted to communicate with a source of lavage liquid; and a trocar plug having a tapered distal end and the trocar plug including a helical groove with a proximal and distal end; said trocar plug movably positioned within the barrel passage; said trocar plug movably positioned within the barrel passage and movable between:
      i) an insertion position where the tapered distal end of the trocar plug extends from the distal end of the barrel;
      ii) an irrigation position where the first opening of the irrigation conduit is in communication with the barrel passage and the trocar plug covers a majority of the drain opening; and
      iii) a flushing position where the trocar plug covers less of the drain opening than when the trocar plug is in the irrigation position; and wherein the helical groove of the trocar plug is traversed by the tab of the barrel as the trocar plug moves between the insertion, irrigation and flushing positions; where the proximal end of the groove serves as a stop when the trocar plug is in the insertion position and the distal end of the groove serves as a stop that prevents removal of the trocar plug from the barrel passage when the trocar plug is in the flushing position,
   b. placing the second opening of the irrigation conduit in communication with a source of lavage liquid;
   c. placing the trocar plug in the insertion position;
   d. inserting the distal end and a portion of the barrel of the fecal collection device into an anal canal of a patient;
   e. moving the trocar plug into the irrigation position;
   f. introducing lavage liquid into a rectum of the patient through the irrigation conduit and the barrel passage of the fecal collection device; and
   g. moving the trocar plug into the flushing position and draining fecal matter and lavage liquid from the rectum of the patient through the barrel passage and the waste drain passage of the fecal collection device.

14. The fecal collection method of claim 13 wherein steps e. and g. include grasping a proximal end portion of the trocar plug.

15. The fecal collection method of claim 13 wherein steps e. and g. include rotating the trocar plug about a longitudinal axis of the trocar plug.

16. A fecal collection system comprising:
   a. a source of lavage liquid; and
   b. a fecal collection device comprising:
      i) a barrel having a distal end, a proximal end and defining a barrel passage therebetween; wherein the barrel comprises a tab positioned within the barrel passage;

ii) a waste drain conduit defining a waste drain passage attached to the barrel so that a drain opening is defined between the barrel passage and the waste drain passage;

iii) an irrigation conduit having a first opening and a second opening where the second opening is in communication with the source of lavage liquid;

iv) a trocar plug having a tapered distal end and the trocar plug including a helical groove with a proximal and distal end;

v) said trocar plug movably positioned within the barrel passage and movable between: an insertion position where the tapered distal end of the trocar plug extends from the distal end of the barrel; an irrigation position where the first opening of the irrigation conduit is in communication with the barrel passage and the trocar plug covers a majority of the drain opening; and a flushing position where the trocar plug covers less of the drain opening than when the trocar plug is in the irrigation position; and wherein the helical groove of the trocar plug is traversed by the tab of the barrel as the trocar plug moves between the insertion, irrigation and flushing positions; where the proximal end of the groove serves as a stop when the trocar plug is in the insertion position and the distal end of the groove serves as a stop that prevents removal of the trocar plug from the barrel passage when the trocar plug is in the flushing position.

17. The fecal collection system of claim 16 further comprising a waste collection container in communication with the waste drain passage.

\* \* \* \* \*